(12) United States Patent
Bennett et al.

(10) Patent No.: US 11,857,433 B2
(45) Date of Patent: *Jan. 2, 2024

(54) SIX DEGREE SPINE STABILIZATION DEVICES AND METHODS

(71) Applicant: GLOBUS MEDICAL, INC., Audubon, PA (US)

(72) Inventors: Jeff Bennett, Pottstown, PA (US); Edward Dwyer, Lehighton, PA (US)

(73) Assignee: Globus Medical, Inc., Audubon, PA (US)

( * ) Notice: Subject to any disclaimer, the term of this patent is extended or adjusted under 35 U.S.C. 154(b) by 34 days.

This patent is subject to a terminal disclaimer.

(21) Appl. No.: 17/748,159

(22) Filed: May 19, 2022

(65) Prior Publication Data

US 2022/0273457 A1 Sep. 1, 2022

Related U.S. Application Data

(60) Continuation of application No. 16/877,572, filed on May 19, 2020, now Pat. No. 11,357,639, which is a
(Continued)

(51) Int. Cl.
*A61F 2/44* (2006.01)
*A61F 2/30* (2006.01)

(52) U.S. Cl.
CPC ............ *A61F 2/4425* (2013.01); *A61F 2/442* (2013.01); *A61F 2002/30011* (2013.01); *A61F 2002/30014* (2013.01); *A61F 2002/30069* (2013.01); *A61F 2002/3081* (2013.01); *A61F 2002/30385* (2013.01); *A61F 2002/30392* (2013.01); *A61F 2002/30393* (2013.01); *A61F 2002/30398* (2013.01); *A61F 2002/30433* (2013.01); *A61F 2002/30448* (2013.01);
(Continued)

(58) Field of Classification Search
CPC .......... A61F 2/44; A61F 2/442; A61F 2/4425; A61F 2/46; A61F 2/4603; A61F 2/4611; A61F 2002/4435; A61F 2002/444
See application file for complete search history.

(56) References Cited

U.S. PATENT DOCUMENTS 3,867,728 A 2/1975 Stubstad et al.
4,309,777 A * 1/1982 Patil ........................ A61F 2/442
606/907

(Continued)

FOREIGN PATENT DOCUMENTS

DE 102009027371 A1 * 1/2010 ........... A61F 2/4425
JP 2012115683 A * 6/2012 ........... A61F 2/0811
WO 2010000766 A2 1/2010

*Primary Examiner* — Eric S Gibson (57) ABSTRACT

An implant stabilizes two adjacent bones of a joint, while enabling a natural kinematic relative movement of the bones. Support components are connected to each bone of the joint, and a flexible core is interposed between them. The core and at least one of the support components are provided with a smooth sliding surface upon which the core and support component may slide relative to each other, enabling a corresponding movement of the bones. The surfaces may have a mating curvature, to mimic a natural movement of the joint. The core is resilient, and may bend or compress, enabling the bones to move towards each other, and or to bend relative to each other.

9 Claims, 4 Drawing Sheets

Related U.S. Application Data continuation of application No. 16/116,989, filed on Aug. 30, 2018, now Pat. No. 10,687,958, which is a continuation of application No. 15/246,779, filed on Aug. 25, 2016, now Pat. No. 10,092,411, which is a continuation of application No. 14/637,430, filed on Mar. 4, 2015, now Pat. No. 9,452,060, which is a division of application No. 13/033,404, filed on Feb. 23, 2011, now Pat. No. 8,998,991.

(52) U.S. Cl.
CPC ............ *A61F 2002/30462* (2013.01); *A61F 2002/30607* (2013.01); *A61F 2002/30616* (2013.01); *A61F 2002/30649* (2013.01); *A61F 2002/30652* (2013.01); *A61F 2002/30658* (2013.01); *A61F 2002/30673* (2013.01); *A61F 2002/30772* (2013.01); *A61F 2002/30878* (2013.01); *A61F 2002/30906* (2013.01); *A61F 2002/30925* (2013.01); *A61F 2002/443* (2013.01); *A61F 2310/00011* (2013.01); *A61F 2310/00023* (2013.01); *A61F 2310/00029* (2013.01); *A61F 2310/00059* (2013.01); *A61F 2310/0097* (2013.01); *A61F 2310/00179* (2013.01); *A61F 2310/00407* (2013.01); *A61F 2310/00976* (2013.01)

(56) References Cited

U.S. PATENT DOCUMENTS

| | | | | |
|---|---|---|---|---|
| 4,997,432 A * | 3/1991 | Keller | A61B 17/2804 600/219 |
| 5,401,269 A * | 3/1995 | Buttner-Janz | A61F 2/4425 606/247 |
| 5,458,642 A * | 10/1995 | Beer | A61F 2/4425 606/247 |
| 5,507,816 A * | 4/1996 | Bullivant | A61F 2/4425 606/247 |
| 5,556,431 A * | 9/1996 | Buttner-Janz | A61F 2/4425 606/247 |
| 5,776,202 A * | 7/1998 | Copf | A61F 2/4225 623/19.12 |
| 5,888,226 A * | 3/1999 | Rogozinski | A61F 2/4425 623/17.16 |
| 5,899,941 A * | 5/1999 | Nishijima | A61F 2/4425 623/17.15 |
| 6,146,421 A * | 11/2000 | Gordon | A61F 2/4425 623/17.15 |
| 6,368,350 B1 * | 4/2002 | Erickson | A61F 2/4425 623/17.14 |
| 6,468,310 B1 * | 10/2002 | Ralph | A61F 2/4425 623/17.13 |
| 6,517,580 B1 * | 2/2003 | Ramadan | A61F 2/4425 623/17.14 |
| 6,682,562 B2 * | 1/2004 | Viart | A61F 2/4425 623/17.14 |
| 6,726,720 B2 * | 4/2004 | Ross | A61F 2/442 623/17.13 |
| 6,770,095 B2 * | 8/2004 | Grinberg | A61F 2/4425 623/17.14 |
| 6,936,071 B1 * | 8/2005 | Marnay | A61F 2/30749 623/17.14 |
| 6,966,929 B2 * | 11/2005 | Mitchell | A61F 2/4425 623/17.11 |
| 6,986,789 B2 * | 1/2006 | Schultz | A61F 2/4425 623/17.15 |
| 7,048,764 B2 * | 5/2006 | Ferree | A61F 2/4425 623/17.15 |
| 7,060,099 B2 * | 6/2006 | Carli | A61F 2/4425 623/17.14 |
| 7,115,146 B2 * | 10/2006 | Boyer, II | A61F 2/30942 623/23.63 |
| 7,204,852 B2 * | 4/2007 | Marnay | A61F 2/4425 606/53 |
| 7,255,714 B2 * | 8/2007 | Malek | A61F 2/44 623/17.14 |
| 7,273,496 B2 * | 9/2007 | Mitchell | A61F 2/4425 623/17.14 |
| 7,326,250 B2 * | 2/2008 | Beaurain | A61F 2/4611 606/86 A |
| 7,407,513 B2 * | 8/2008 | Alleyne | A61F 2/4405 606/246 |
| 7,442,211 B2 * | 10/2008 | de Villiers | A61F 2/4611 623/17.14 |
| 7,537,615 B2 * | 5/2009 | Lemaire | A61F 2/4425 623/17.14 |
| 7,563,286 B2 * | 7/2009 | Gerber | A61F 2/4425 623/17.14 |
| 7,575,599 B2 * | 8/2009 | Villiers | A61F 2/442 623/17.14 |
| 7,582,115 B2 * | 9/2009 | Weber | A61F 2/4425 623/17.14 |
| 7,670,377 B2 * | 3/2010 | Zucherman | A61F 2/4425 623/17.15 |
| 7,708,760 B2 * | 5/2010 | Parsons | A61B 17/70 606/247 |
| 7,708,776 B1 * | 5/2010 | Blain | A61F 2/4425 623/908 |
| 7,708,777 B2 * | 5/2010 | O'Neil | A61F 2/4425 623/17.13 |
| 7,713,304 B2 * | 5/2010 | Ankney | A61B 17/1671 623/17.15 |
| 7,717,959 B2 * | 5/2010 | William | A61F 2/4425 623/17.15 |
| 7,731,754 B2 * | 6/2010 | de Villiers | A61F 2/4425 623/17.14 |
| 7,753,956 B2 * | 7/2010 | de Villiers | A61F 2/4611 623/17.14 |
| 7,799,083 B2 * | 9/2010 | Smith | A61F 2/34 623/17.16 |
| 7,803,162 B2 * | 9/2010 | Marnay | A61F 2/4425 623/17.16 |
| 7,833,273 B2 * | 11/2010 | Buettner-Janz | A61F 2/4425 623/17.14 |
| 7,837,734 B2 * | 11/2010 | Zucherman | A61F 2/4425 623/17.15 |
| 7,842,088 B2 * | 11/2010 | Rashbaum | A61F 2/4425 623/17.14 |
| 7,850,735 B2 * | 12/2010 | Eisermann | A61B 17/1671 606/279 |
| 7,905,919 B2 * | 3/2011 | Kellar | A61F 2/38 623/22.3 |
| 7,909,876 B2 * | 3/2011 | Dooris | A61F 2/4425 623/17.14 |
| 7,927,373 B2 * | 4/2011 | Parsons | A61F 2/4611 606/86 A |
| 7,927,374 B2 * | 4/2011 | Duggal | A61F 2/4425 623/17.14 |
| 7,959,678 B2 * | 6/2011 | Filippi | A61F 2/4425 623/17.14 |
| 8,002,834 B2 * | 8/2011 | de Villiers | A61F 2/4425 623/17.14 |
| 8,052,754 B2 * | 11/2011 | Froehlich | A61F 2/4425 623/17.15 |
| 8,083,797 B2 * | 12/2011 | Villiers | A61F 2/4425 623/17.13 |
| 8,163,025 B2 * | 4/2012 | Belliard | A61F 2/4425 623/17.15 |
| 8,167,948 B2 * | 5/2012 | Paul | A61B 17/1671 623/17.16 |
| 8,231,677 B2 * | 7/2012 | Duggal | A61F 2/4425 623/17.14 |
| 8,257,439 B2 * | 9/2012 | Zeegers | A61F 2/4425 623/17.14 |
| 8,267,999 B2 * | 9/2012 | Beaurain | A61F 2/4425 623/17.14 |

(56) References Cited

U.S. PATENT DOCUMENTS

| | | | | |
|---|---|---|---|---|
| 8,277,505 B1* | 10/2012 | Doty | A61F 2/4425 | 623/17.14 |
| 8,277,508 B2* | 10/2012 | Trieu | A61F 2/442 | 623/17.15 |
| 8,277,509 B2* | 10/2012 | Hansell | A61F 2/442 | 623/17.16 |
| 8,303,661 B2* | 11/2012 | Keller | A61F 2/4425 | 623/17.16 |
| 8,323,323 B2* | 12/2012 | Aeschlimann | B29C 66/126 | 606/300 |
| 8,349,017 B2* | 1/2013 | Marnay | A61F 2/4425 | 606/86 A |
| 8,496,713 B2* | 7/2013 | Bennett | A61F 2/442 | 623/18.11 |
| 8,998,991 B2* | 4/2015 | Bennett | A61F 2/442 | 623/17.16 |
| 9,452,060 B2* | 9/2016 | Bennett | A61F 2/442 | |
| 10,092,411 B2* | 10/2018 | Bennett | A61F 2/442 | |
| 10,687,958 B2* | 6/2020 | Bennett | A61F 2/4425 | |
| 11,357,639 B2* | 6/2022 | Bennett | A61F 2/4425 | |
| 2002/0035400 A1* | 3/2002 | Bryan | A61F 2/4425 | 623/17.15 |
| 2003/0191534 A1* | 10/2003 | Viart | A61F 2/4425 | 623/17.15 |
| 2003/0204261 A1* | 10/2003 | Eisermann | A61F 2/4425 | 623/17.14 |
| 2003/0208271 A1* | 11/2003 | Kuras | A61F 2/442 | 623/17.11 |
| 2003/0208273 A1* | 11/2003 | Eisermann | A61F 2/4425 | 623/17.14 |
| 2004/0010316 A1* | 1/2004 | William | A61F 2/4425 | 623/17.11 |
| 2004/0102846 A1* | 5/2004 | Keller | A61F 2/4425 | 623/17.11 |
| 2004/0111160 A1* | 6/2004 | Evans | A61L 31/048 | 623/17.14 |
| 2004/0117022 A1* | 6/2004 | Marnay | A61F 2/30771 | 623/17.15 |
| 2004/0138750 A1* | 7/2004 | Mitchell | A61F 2/4425 | 623/17.11 |
| 2004/0143332 A1* | 7/2004 | Krueger | A61B 17/1604 | 606/90 |
| 2004/0153157 A1* | 8/2004 | Keller | A61F 2/4425 | 623/17.14 |
| 2004/0158328 A1* | 8/2004 | Eisermann | A61B 17/1757 | 623/17.11 |
| 2004/0172135 A1* | 9/2004 | Mitchell | A61F 2/4425 | 623/17.15 |
| 2004/0220668 A1* | 11/2004 | Eisermann | A61B 17/1642 | 623/17.11 |
| 2004/0225365 A1* | 11/2004 | Eisermann | A61F 2/4425 | 623/17.14 |
| 2004/0243240 A1* | 12/2004 | Beaurain | A61F 2/4425 | 606/90 |
| 2005/0004572 A1* | 1/2005 | Biedermann | A61F 2/44 | 606/247 |
| 2005/0021145 A1* | 1/2005 | de Villiers | A61F 2/4611 | 623/17.14 |
| 2005/0033437 A1* | 2/2005 | Bao | A61F 2/4684 | 623/17.15 |
| 2005/0043802 A1* | 2/2005 | Eisermann | A61B 17/1642 | 623/17.11 |
| 2005/0085917 A1* | 4/2005 | Marnay | A61F 2/30749 | 623/17.11 |
| 2005/0125061 A1* | 6/2005 | Zucherman | A61F 2/4425 | 623/17.11 |
| 2005/0131543 A1* | 6/2005 | Benzel | A61F 2/4611 | 623/17.13 |
| 2005/0165485 A1* | 7/2005 | Trieu | A61F 2/442 | 623/17.13 |
| 2005/0187631 A1* | 8/2005 | Van Hoeck | A61F 2/442 | 623/17.13 |
| 2005/0203626 A1* | 9/2005 | Sears | A61F 2/4425 | 623/17.11 |
| 2005/0251260 A1* | 11/2005 | Gerber | A61F 2/4425 | 623/17.13 |
| 2005/0251261 A1* | 11/2005 | Peterman | A61F 2/4425 | 623/908 |
| 2005/0261772 A1* | 11/2005 | Filippi | A61F 2/4425 | 623/17.13 |
| 2005/0283245 A1* | 12/2005 | Gordon | A61F 2/4425 | 623/908 |
| 2006/0015183 A1* | 1/2006 | Gilbert | A61F 2/4425 | 623/17.11 |
| 2006/0036325 A1* | 2/2006 | Paul | A61F 2/442 | 623/17.14 |
| 2006/0041314 A1* | 2/2006 | Millard | A61F 2/4425 | 623/17.15 |
| 2006/0111783 A1* | 5/2006 | Aflatoon | A61F 2/4425 | 623/17.14 |
| 2006/0116768 A1* | 6/2006 | Krueger | A61B 17/1604 | 606/90 |
| 2006/0178744 A1* | 8/2006 | de Villiers | A61F 2/4425 | 623/17.13 |
| 2006/0190082 A1* | 8/2006 | Keller | A61F 2/4425 | 623/17.11 |
| 2006/0195192 A1* | 8/2006 | Gordon | A61B 17/7052 | 606/247 |
| 2006/0229725 A1* | 10/2006 | Lechmann | A61F 2/4425 | 623/17.11 |
| 2006/0235527 A1* | 10/2006 | Buettner-Janz | A61F 2/4425 | 623/17.14 |
| 2006/0247777 A1* | 11/2006 | Stamp | A61F 2/4425 | 623/17.14 |
| 2006/0276907 A1* | 12/2006 | Boyer | A61F 2/28 | 623/23.51 |
| 2006/0293752 A1* | 12/2006 | Moumene | A61F 2/4425 | 623/17.13 |
| 2006/0293754 A1* | 12/2006 | deVilliers | A61F 2/4425 | 623/17.14 |
| 2007/0010826 A1* | 1/2007 | Rhoda | A61F 2/4425 | 606/99 |
| 2007/0055378 A1* | 3/2007 | Ankney | A61F 2/442 | 623/908 |
| 2007/0073406 A1* | 3/2007 | Gordon | A61B 17/7005 | 623/17.15 |
| 2007/0162137 A1* | 7/2007 | Kloss | A61F 2/4425 | 623/17.15 |
| 2007/0168037 A1* | 7/2007 | Posnick | A61F 2/4425 | 623/17.14 |
| 2007/0173936 A1* | 7/2007 | Hester | A61F 2/4425 | 623/17.11 |
| 2007/0173941 A1* | 7/2007 | Allard | A61F 2/4425 | 623/17.14 |
| 2007/0173942 A1* | 7/2007 | Heinz | A61F 2/4425 | 623/17.15 |
| 2007/0191955 A1* | 8/2007 | Zucherman | A61F 2/4425 | 623/17.15 |
| 2007/0233255 A1* | 10/2007 | Song | A61F 2/4425 | 623/17.11 |
| 2007/0260317 A1* | 11/2007 | Ankney | A61B 17/1671 | 623/17.15 |
| 2007/0299524 A1* | 12/2007 | Rivin | A61F 2/4425 | 623/17.13 |
| 2008/0051900 A1* | 2/2008 | de Villiers | A61F 2/442 | 606/86 A |
| 2008/0133011 A1* | 6/2008 | de Villiers | A61F 2/4611 | 623/17.11 |
| 2008/0133013 A1* | 6/2008 | Duggal | A61F 2/4425 | 623/17.14 |
| 2008/0140204 A1* | 6/2008 | Heinz | A61F 2/4611 | 623/17.15 |
| 2008/0161923 A1* | 7/2008 | Parsons | A61F 2/4425 | 623/17.14 |
| 2008/0183296 A1* | 7/2008 | Ferree | A61F 2/4425 | 623/17.14 |
| 2008/0215155 A1* | 9/2008 | de Villiers | A61F 2/4425 | 623/17.11 |

(56) References Cited

U.S. PATENT DOCUMENTS

| | | | | |
|---|---|---|---|---|
| 2008/0221696 A1* | 9/2008 | de Villiers | ............ | A61F 2/4611 623/17.15 |
| 2008/0228274 A1* | 9/2008 | De Villiers | ......... | A61F 2/30771 623/17.14 |
| 2008/0228277 A1* | 9/2008 | de Villiers | ............ | A61F 2/4611 623/17.16 |
| 2008/0234686 A1* | 9/2008 | Beaurain | ............... | A61F 2/4425 606/90 |
| 2008/0243253 A1* | 10/2008 | Levieux | ............... | A61F 2/4425 623/17.15 |
| 2008/0300688 A1* | 12/2008 | Cannon | ............... | A61F 2/4425 623/17.14 |
| 2009/0043391 A1* | 2/2009 | de Villiers | ............ | A61F 2/4425 623/17.15 |
| 2009/0069894 A1* | 3/2009 | Duggal | ................ | A61F 2/4425 623/17.11 |
| 2009/0076614 A1* | 3/2009 | Arramon | ............... | A61F 2/4425 623/17.11 |
| 2009/0088853 A1* | 4/2009 | Ogilvie | ................... | A61F 2/442 623/17.11 |
| 2009/0192617 A1* | 7/2009 | Arramon | ............... | A61F 2/4425 623/17.13 |
| 2009/0204219 A1* | 8/2009 | Beaurain | ............... | A61F 2/4425 623/17.16 |
| 2009/0210060 A1* | 8/2009 | de Villiers | ............ | A61F 2/442 623/17.14 |
| 2009/0222101 A1* | 9/2009 | de Villiers | ............ | A61F 2/4425 623/17.16 |
| 2009/0234458 A1* | 9/2009 | de Villiers | ............ | A61F 2/4425 623/17.15 |
| 2009/0270989 A1* | 10/2009 | Conner | ............. | A61B 17/1671 606/191 |
| 2009/0270992 A1* | 10/2009 | Gerber | ................. | A61F 2/4425 623/17.13 |
| 2009/0276051 A1* | 11/2009 | Arramon | ................ | C08L 71/00 623/17.15 |
| 2009/0281629 A1* | 11/2009 | Roebling | ............. | A61F 2/4425 623/17.14 |
| 2009/0326656 A1* | 12/2009 | de Villiers | ............ | A61F 2/4425 623/17.15 |
| 2010/0004746 A1* | 1/2010 | Arramon | ............... | A61F 2/4425 623/17.15 |
| 2010/0004749 A1* | 1/2010 | Beger | ................... | A61F 2/4425 623/17.16 |
| 2010/0030335 A1* | 2/2010 | Arramon | ................... | A61F 2/36 623/17.13 |
| 2010/0030338 A1* | 2/2010 | Simon | ...................... | A61F 2/44 623/17.16 |
| 2010/0042220 A1* | 2/2010 | Tauber | ................. | A61F 2/4425 623/17.16 |
| 2010/0057205 A1* | 3/2010 | Justin | .................. | A61F 2/4455 606/86 R |
| 2010/0076558 A1* | 3/2010 | de Villiers | ............ | A61F 2/4611 606/86 R |
| 2010/0082110 A1* | 4/2010 | Belliard | ................ | A61F 2/4425 623/17.16 |
| 2010/0087868 A1* | 4/2010 | Barr | ....................... | A61F 2/4425 606/279 |
| 2010/0094427 A1* | 4/2010 | Bertagnoli | ............ | A61F 2/4425 623/17.16 |
| 2010/0137992 A1* | 6/2010 | Buttner-Janz | ......... | A61F 2/4425 623/17.16 |
| 2010/0168860 A1* | 7/2010 | Reichen | ................ | A61F 2/4611 623/17.15 |
| 2010/0191338 A1* | 7/2010 | de Villiers | ............ | A61F 2/4425 623/17.16 |
| 2010/0217395 A1* | 8/2010 | Bertagnoli | ............ | A61B 17/144 606/82 |
| 2010/0228351 A1* | 9/2010 | Ankney | ............. | A61B 17/1671 623/17.16 |
| 2010/0249936 A1* | 9/2010 | Bertagnoli | ............... | A61F 2/442 606/279 |
| 2010/0256762 A1* | 10/2010 | Bertagnoli | ............... | A61F 2/442 623/17.16 |
| 2010/0256763 A1* | 10/2010 | Sournac | ................ | A61F 2/4425 623/17.16 |
| 2010/0280617 A1* | 11/2010 | Coppes | ................. | A61F 2/4425 623/17.16 |
| 2010/0286784 A1* | 11/2010 | Curran | ................ | A61F 2/30771 623/17.16 |
| 2010/0292800 A1* | 11/2010 | Zubok | ................. | A61F 2/4425 623/17.16 |
| 2010/0298939 A1* | 11/2010 | Delfosse | ............... | A61F 2/4425 623/17.16 |
| 2010/0312347 A1* | 12/2010 | Arramon | ................. | A61L 27/18 623/17.16 |
| 2010/0324684 A1* | 12/2010 | Eisermann | ............ | A61F 2/4425 606/264 |
| 2011/0004313 A1* | 1/2011 | de Villiers | ............ | A61F 2/4425 623/17.16 |
| 2011/0022177 A1* | 1/2011 | Yeh | ....................... | A61F 2/4425 623/17.15 |
| 2011/0054618 A1* | 3/2011 | Lechmann | ............ | A61F 2/4425 623/17.16 |
| 2011/0082556 A1* | 4/2011 | Duggal | ................. | A61F 2/4657 623/17.16 |
| 2011/0098821 A1* | 4/2011 | Ankney | ............. | A61B 17/1671 606/90 |
| 2011/0106263 A1* | 5/2011 | Eisermann | ......... | A61B 17/1757 623/17.16 |
| 2011/0118845 A1* | 5/2011 | Overes | .................. | A61F 2/4425 623/17.16 |
| 2011/0125270 A1* | 5/2011 | Paul | ....................... | A61F 2/4611 606/86 A |
| 2011/0144754 A1* | 6/2011 | Chee | ........................ | A61F 2/442 623/17.16 |
| 2011/0160862 A1* | 6/2011 | de Villiers | ............ | A61F 2/4425 623/17.16 |
| 2011/0218630 A1* | 9/2011 | Niess | ..................... | C04B 35/119 623/17.16 |
| 2011/0238185 A1* | 9/2011 | Filippi | .................. | A61F 2/4425 264/279 |
| 2011/0251690 A1* | 10/2011 | Berger | ................. | A61F 2/4425 623/17.16 |
| 2011/0257747 A1* | 10/2011 | Copf | ....................... | A61F 2/4425 623/17.15 |
| 2011/0264223 A1* | 10/2011 | Lemaire | ................ | A61F 2/4425 623/17.16 |
| 2011/0295374 A1* | 12/2011 | Bryan | ................... | A61F 2/4425 623/17.16 |
| 2011/0320003 A1* | 12/2011 | Duggal | ................. | A61F 2/4657 623/17.16 |
| 2012/0016480 A1* | 1/2012 | Gerber | ................. | A61F 2/4425 623/17.16 |
| 2012/0035732 A1* | 2/2012 | de Villiers | ............ | A61F 2/4611 623/17.16 |
| 2012/0053694 A1* | 3/2012 | Villiers | ................. | A61F 2/4425 29/428 |
| 2012/0059478 A1* | 3/2012 | de Villiers | ............ | A61F 2/4425 623/17.16 |
| 2012/0101579 A1* | 4/2012 | de Villiers | ............ | A61F 2/4611 623/17.16 |
| 2012/0109316 A1* | 5/2012 | Marnay | ................. | A61F 2/4425 623/17.16 |
| 2012/0130497 A1* | 5/2012 | Taylor | .................. | A61F 2/4611 623/17.16 |
| 2012/0150298 A1* | 6/2012 | Bennett | ................ | A61F 2/4425 623/17.11 |
| 2012/0172988 A1* | 7/2012 | Berger | ................. | A61F 2/4425 623/17.16 |
| 2012/0197406 A1* | 8/2012 | Paul | .................... | A61B 17/1757 623/17.16 |
| 2012/0215314 A1* | 8/2012 | Bennett | ................ | A61F 2/442 623/17.16 |
| 2012/0290093 A1* | 11/2012 | Hansell | ............... | A61F 2/4455 623/17.16 |
| 2012/0310349 A1* | 12/2012 | Gordon | .............. | A61B 17/7007 623/17.16 |

(56) References Cited

U.S. PATENT DOCUMENTS

| | | | |
|---|---|---|---|
| 2013/0013069 A1* | 1/2013 | de Villiers | A61F 2/4425 |
| | | | 623/17.15 |
| 2013/0013072 A1* | 1/2013 | de Villiers | A61F 2/4611 |
| | | | 623/17.16 |
| 2015/0173912 A1* | 6/2015 | Bennett | A61F 2/442 |
| | | | 623/17.16 |
| 2017/0035575 A1* | 2/2017 | Bennett | A61F 2/4425 |
| 2019/0008652 A1* | 1/2019 | Bennett | A61F 2/4425 |
| 2020/0276027 A1* | 9/2020 | Bennett | A61F 2/4425 |
| 2022/0273457 A1* | 9/2022 | Bennett | A61F 2/442 |

* cited by examiner

SIX DEGREE SPINE STABILIZATION DEVICES AND METHODS

CROSS REFERENCE TO RELATED APPLICATION

This application is a continuation of U.S. patent application Ser. No. 16/877,572, filed May 19, 2020 (published as U.S. Pat. Pub. No. 2020-0276027), which is a continuation of U.S. patent application Ser. No. 16/116,989, filed Aug. 30, 2018, now. U.S. Pat. No. 10,687,958, which is a continuation of U.S. patent application Ser. No. 15/246,779, filed Aug. 25, 2016, now U.S. Pat. No. 10,092,411, which is a continuation of U.S. patent application Ser. No. 14/637,430 filed on Mar. 4, 2015, now U.S. Pat. No. 9,452,060, which is a divisional of U.S. patent application Ser. No. 13/033,404 filed on Feb. 23, 2011, now U.S. Pat. No. 8,998,991, which are each incorporated herein by reference in its entirety for all purposes.

FIELD OF THE INVENTION

This invention relates to stabilizing adjacent vertebrae of the spine, after surgery or trauma, while preserving a natural kinematic signature.

BACKGROUND OF THE INVENTION

Intervertebral devices are used to address diseases or disorders of the spine, or to address damage due to trauma. These devices operate, for example, to stabilize, guide, or limit movement of adjacent vertebrae, while bearing weight.

The spinal disc may be displaced or damaged due to trauma, disease, degenerative defects, or wear over an extended period. A disc herniation occurs when the annulus fibers are weakened or torn and the inner tissue of the nucleus becomes permanently bulged, distended, or extruded out of its normal, internal annulus confines. The mass of a herniated or "slipped" nucleus tissue can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases causing the annulus to buckle in areas where the laminated plies are loosely bonded. As these overlapping laminated plies of the annulus begin to buckle and separate, either circumferential or radial annular tears may occur, which may contribute to persistent or disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate back pain from degenerated or herniated discs, the nucleus is removed and the two adjacent vertebrae are surgically fused together. While this treatment alleviates the pain, all discal motion is lost in the fused segment. Ultimately, this procedure places a greater stress on the discs adjacent to the fused segment as they compensate for lack of motion, perhaps leading to premature degeneration of those adjacent disc.

As an alternative to vertebral fusion, various prosthetic discs have been developed. The first prosthetics embodied a wide variety of ideas, such as ball bearings, springs, metal spikes and other perceived aids. These prosthetics are all made to replace the entire intervertebral disc space and are large and rigid. Many of the current designs for prosthetic discs are large and inflexible. In addition, prosthetic disc sizes and other parameters limit the approach a surgeon may take to implant the devices.

There is a need for a novel spinal disc that mimics the motion of the natural spinal disc.

SUMMARY OF THE INVENTION

An implant in accordance with the invention includes a flexible core, a first support component, operative to contact a first engaging surface of the core, and a second support component, operative to contact a second, opposing engaging surface of the core.

The implant of the invention is operative, when positioned between adjacent bones of a joint, such as adjacent vertebrae, to stabilize the joint. The implant further enables a natural kinematic movement of the joint, while limiting movement beyond a therapeutic range of motion.

A flexible core is provided with an inflection region of greater flexibility, which enables a displacement or changed orientation of opposed engaging surfaces of the core. In one embodiment, the core tapers at one end to form the inflection region, and which may deform or buckle to enable a relative angular displacement of engaging surfaces.

In addition, the core may compress to reduce a distance between portions of first and second engaging surfaces. Compression may include an expansion of material outwards relative to an interior of the core, or material of the core may collapse into an interior.

A tether, or lanyard may be provided, operative to limit a maximum displacement of the core and one or both of the first and second support components. The lanyard is affixed to two of either core and one or both support components. The lanyard is formed of a flexible material which does not prevent movement within an intended range of motion of the implant, and may advantageously be formed of a resilient material, to avoid an abrupt relative cessation of movement at a limit of travel.

Each support component includes an engagement plate having a core engaging surface and a bone engaging surface. A keel or other projection extends from the bone engaging surface, and is operative to engage a bony surface, for example, an interior portion of a vertebra. The projection may include a bone ingrowth surface, region, or spaces, to further secure the plate into engagement with the bone. Core engaging surfaces of the first and second support component are advantageously formed with a lubricious material relative to a surface material of the engaging surfaces of the core, if sliding or rotating relative to the core is intended.

In one embodiment, an inflection region of the core is most flexible at a point proximate an engaging surface. A hollow interior may be included, operative to provide a space into which material forming the inflection region may deflect. A core engaging surface is provided with a smooth surface, upon which a second engaging surface of the flexible core may slide.

Figure 4:
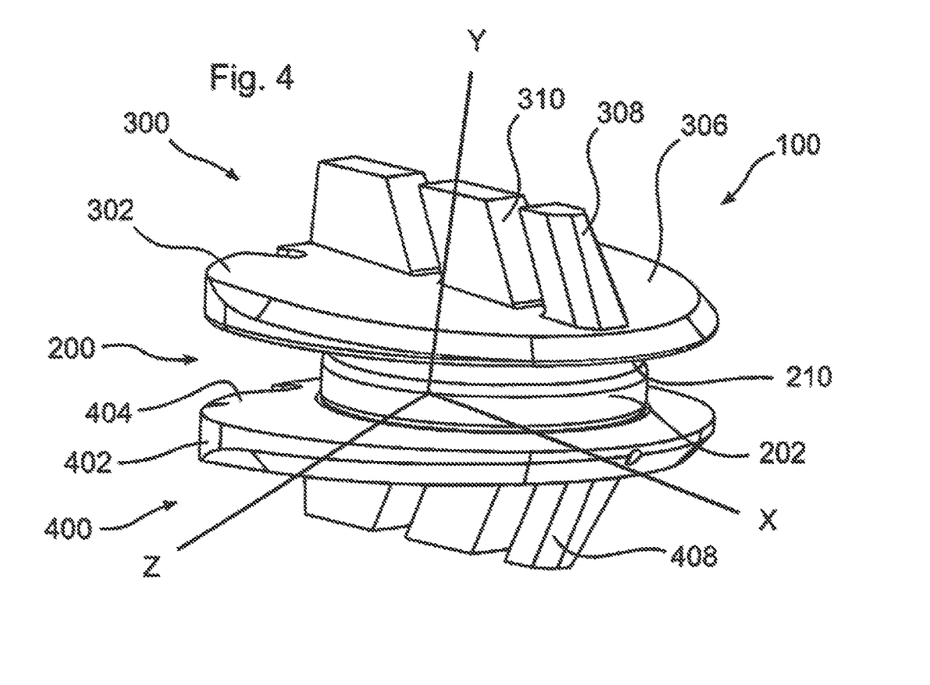
FIG. 4 illustrates the implant of FIG. 1, with lines indicating degrees of motion of the implant.

Relative motion of bones, for example opposing bones of a joint, result from movement of a patient into which an implant of the invention is implanted. As the first and second support components are attached to these bones, a corresponding motion is induced in the support components. In the natural body of the patient, these bones move in accordance with six degrees of motion. Each of these degrees of motion are enabled with an implanted implant of the invention, as follows, with reference to FIG. 4:

(1) translation in the direction indicated by line "X", corresponding to the core sliding along an engaging surface;

(2) translation in the direction indicated by line "Y", corresponding to axial compression of the core;

(3) translation in the direction indicated by line "Z", corresponding to the core sliding along an engaging surface;

(4) rotation about an axis indicated by line "X", corresponding to compression of one side of the core;

(5) rotation about an axis indicated by line "Y", corresponding to the corerotating upon an engaging surface; and (6) rotation about an axis indicated by line "Z", corresponding to compression of one side of the core.

Alternatively stated, if an axis of the implant is defined as extending through an implant of the invention from a first adjacent bone to a second adjacent bone, the implant would enable relative motion of the first and second adjacent bones with respect to:

(a) opposite rotation about the axis;

(b) axially bending;

(c) axially compressing; and (d) radial sliding with respect to the axis.

In an alternative embodiment, the core includes first and second segments separated by an inflection region that is substantially narrower than flanking segments, and thus bends to enable an angular displacement of the segments and their associated engaging surfaces.

In one embodiment of the invention, at least a portion of the support component has a core engaging surface configured as a curved smooth surface which slidably engages a mating region of the core. A curved slidable portion of the core engaging surface is recessed within a support component, and a mating slidable portion of an engaging surface projects from the core; alternatively, the core engaging surface may be projected, and an engaging surface of the core may be recessed.

Similarly, both sides of the core may be curved, each side mateable with a curved surface of a support component, for example, forming two convex surfaces. Mating surfaces on both sides of the core, for example, operate to foster a desired kinematic movement, and maintain a desired ligament tension throughout the expected range of motion. It should be understood, however, that in accordance with the invention, either surface may be either convex, concave, or flat, as the therapeutic needs of the patient dictate. In use, a configuration with a curved mating surface enables all six degrees of movement as described above, however, due to the mating curved slidable engaging surfaces, additional directional stability is provided.

In a further embodiment, the core is provided with a flat surface at a second engaging surface, which is matably connectable to a flat core engaging surface of a support component. One or more pins pass through pin bores or apertures provided in the core and support component, locking the two components together. In addition, a snap fit engagement between recessed and projecting portions of the core and a support component may be provided to further secure the core and support component together.

In yet another embodiment of the invention, the core engaging surface has a curved portion having a radius which is larger than a curved portion of a mating portion of the core. As such, the core may slide relative to the support component. The core may at the same time be rotated, and compressed evenly or laterally.

Mating surfaces of the core and a support component may include concave, convex, semi-spherical, or barrel shapes, whereby a resistance to sliding, spinning, rotating, rocking, or other relative movement may be uniform in all directions, or different in specific directions.

The invention provides a joint replacement implant, for example for replacement or stabilization of a cervical disc replacement, although other joints may be partially or completely replaced by the implant, for example one or more joints of the fingers, hand, wrist, elbow, shoulder, other areas of the spine, hip, knee, ankle, foot, or toes.

Implants of the invention are operative to restore the natural kinematic signature and natural joint properties, particularly for spinal discs, but for all joints which exhibit movement in all six degrees of motion, as detailed above.

All elements of implant may be made from a flexible material, although the core, in particular, flexes in order to accommodate an angular displacement of first and second support components. As the joint is flexed or extended, the flexible and or resilient material of the core may bulge or stretch to enable an angular displacement of opposing engaging surfaces. Additionally, or alternatively, an inflection region provides a relatively weaker region of the core, which is adapted through thickness and or shape to facilitate bending of the core.

Implant may be fabricated using any biocompatible and materials known to one skilled in the art, having sufficient strength, flexibility, resiliency, and durability for the patient, and for the term during which the device is to be implanted.

In accordance with the invention, a single implant may be used, to provide stabilization for a weakened joint or joint portion. Alternatively, two, three, or more implants may be used, at a single joint level, or in multiple joints. Moreover, implants of the invention may be combined with other stabilizing means.

Any surface or component of the invention may be coated with or impregnated with therapeutic agents, including bone growth, healing, antimicrobial, or drug materials, which may be released at a therapeutic rate, using methods known to those skilled in the art.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

In the description which follows, any reference to direction or orientation is intended primarily and solely for purposes of illustration and is not intended in any way as a limitation to the scope of the present invention. Also, the particular embodiments described herein are not to be considered as limiting of the present invention.

Figure 1:
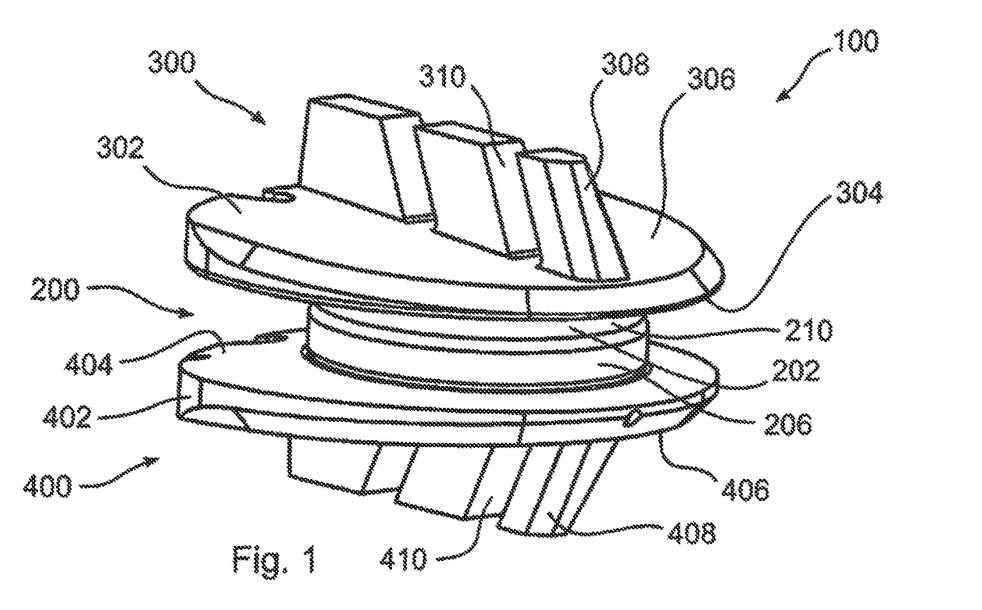
FIG. 1 depicts a perspective view of an implant in accordance with the invention.
Figure 2:
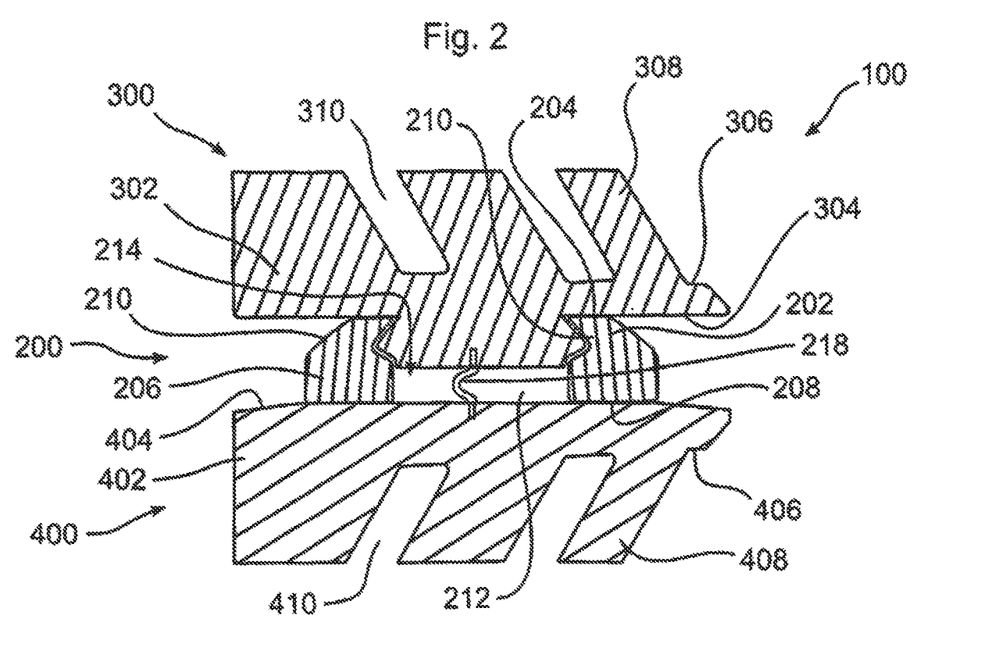
FIG. 2 illustrates a cross section of the implant of FIG. 1, taken centrally through bone engaging projections of the implant.

Referring now to the figures, in which like reference numerals refer to like elements, FIGS. 1 and 2 illustrate an implant 100 in accordance with the invention, including a flexible core 200, a first support component 300, operative to contact a first engaging surface 204 of core 200, and a second support component 400, operative to contact an opposing second engaging surface 208 of core 200.

Figure 3:
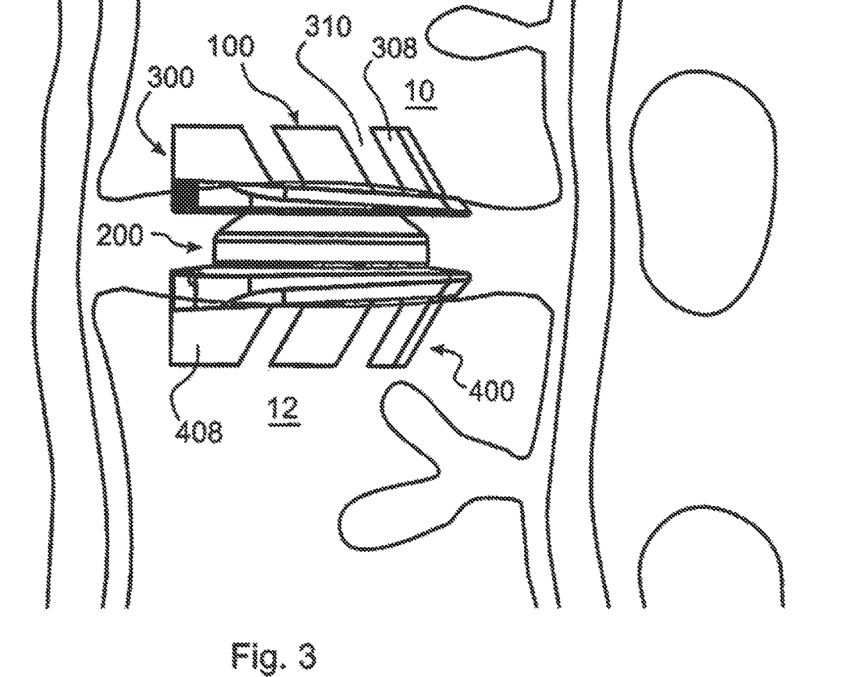
FIG. 3 illustrates the implant of FIG. 1, positioned between two adjacent bones in a body.

With reference to FIG. 3, implant 100 is operative, when positioned between adjacent bones of a joint, such as for example vertebrae 10, 12, to stabilize a joint formed by adjacent vertebrae. Implant 100 further enables natural kinematic movement of the joint while limiting movement beyond a therapeutic range of motion. In one embodiment, this range of motion reflects the complete natural kinematic signature for the patient.

Referring again to FIGS. 1 and 2, flexible core 200 includes a first engaging surface 204 disposed upon a first segment 202, and a second engaging surface 208, disposed upon a second segment 206. In the embodiment shown in FIGS. 1 and 2, flexible core 200 is provided with an inflection region 210 of greater flexibility, which enables a displacement or changed orientation of engaging surface 204 with respect to engaging surface 208. In particular, first segment 202 tapers at one end to form inflection region 210, which may deform or buckle to enable a relative angular displacement of engaging surfaces 204, 208.

In addition, core 200 may compress to reduce a distance between portions of first and second engaging surfaces 204, 208. Compression may include an expansion of material outwards relative to an interior 214 of core 200, resulting in an increase in a diameter of core 200, or material of core 200 may collapse into an interior of core 200, thereby partially or completely maintaining an exterior dimension of core 200. Alternatively, spaces within the material of core 200 may be reduced in size, for example spaces formed by a cellular or porous matrix of the material of core 200 may compress, whereby expansion of an exterior dimension of core 200 may be maintained or limited.

First support component 300 includes an engagement plate 302 having a core engaging surface 304, and a bone engaging surface 306. A keel or other projection 308 extends from bone engaging surface 306, and is operative to engage a bony surface, for example, an interior portion of vertebra 10 or 12. Projection 308 includes bone ingrowth spaces 310, operative to provide an area for bone ingrowth, to further secure plate 302 into engagement with the bone to which plate 302 is attached.

Second support component 400 includes an engagement plate 402 having a core engaging surface 404, and a bone engaging surface 406. A keel, extension, or projection 408 extends from bone engaging surface 406, and is operative to engage a bony surface, for example, an interior portion of vertebra 10 or 12. Projection 408 includes bone ingrowth spaces 410, operative to provide an area for bone ingrowth, to further secure plate 402 into engagement with the bone to which plate 402 is attached.

Bone ingrowth spaces 310, 410 may each advantageously be formed at an angle with respect to a direction of projection 308, 408 insertion, thereby potentially reducing an incidence of separation of implant 100 from the bone, after bone ingrowth has taken place.

Core engaging surfaces 304, 404 of first and second support component 300, 400 are advantageously formed with a lubricious material relative to a surface material of engaging surface 204, 208 of core 200, if sliding or rotating relative to core 200 is intended.

FIG. 2 additionally illustrates a tether, or lanyard 218, operative to limit a maximum displacement of core 200 and one or both of first and second support components 300, 400. Lanyard 218 is affixed to two of either core 200 and one of support components 300, 400, or both support components 300, 400. Lanyard 218 is formed of a flexible material which does not prevent movement within an intended range of motion of implant 100, as described herein, and may advantageously be formed of a resilient material, to avoid an abrupt relative cessation of movement, at a limit of travel, of elements to which it is affixed.

In the embodiment of FIGS. 1-4, inflection region 210 is most flexible at a point proximate engaging surface 204. A hollow interior 212 may be included, operative to provide a space into which material forming region 210 may deflect during displacement of engaging surface 204 relative to engaging surface 208. A tether 218 may be provided, operative to limit a maximum extent of motion of first and second support components 300, 400. In this embodiment, core engaging surface 404 is provided with a smooth surface, upon which a second engaging surface of flexible core 200 may slide. Core engaging surface 404 is illustrated as substantially planar in FIG. 4, although a projection and recess, as described for FIGS. 1 and 2, may alternatively be provided. A lip or raised portion extending from core engaging surface 404, not shown, may further, or in alternative to lanyard 218, operate to limit an extent of movement of engaging surface 208 upon core engaging surface 404.

With reference to FIGS. 3 and 4, relative motion of bones 10 and 12 result from movement of a patient into which implant 100 is implanted. As first and second support components 300, 400 are attached to bones 10, 12, respectively, a corresponding motion is induced in components 300, 400. It should be understood that, in accordance with the invention, component 400 may be connected to bone 10, and component 300 may be connected to bone 12; that is, either component 300 or 400 may be positioned superiorly with respect to the other.

In the natural body of the patient, bones 10 and 12 move in accordance with six degrees of motion. Each of these degrees of motion is enabled with an implanted implant 100, as diagrammed in FIG. 4. Specifically:

(1) translation in the direction indicated by line "X", corresponding to core 200 sliding along engaging surface 404;

(2) translation in the direction indicated by line "Y", corresponding to axial compression of core 200;

(3) translation in the direction indicated by line "Z", corresponding to core 200 sliding along engaging surface 404;

(4) rotation about an axis indicated by line "X", corresponding to compression of one side of core 200;

(5) rotation about an axis indicated by line "Y", corresponding to core 200 rotating upon engaging surface 404; and (6) rotation about an axis indicated by line "Z", corresponding to compression of one side of core 200.

Alternatively stated, if an axis of the implant is defined as extending through an implant of the invention from a first adjacent bone to a second adjacent bone, the implant would enable relative motion of the first and second adjacent bones with respect to:

(a) opposite rotation about the axis;

(b) axially bending;

(c) axially compressing; and (d) radial sliding with respect to the axis.

Figure 5:
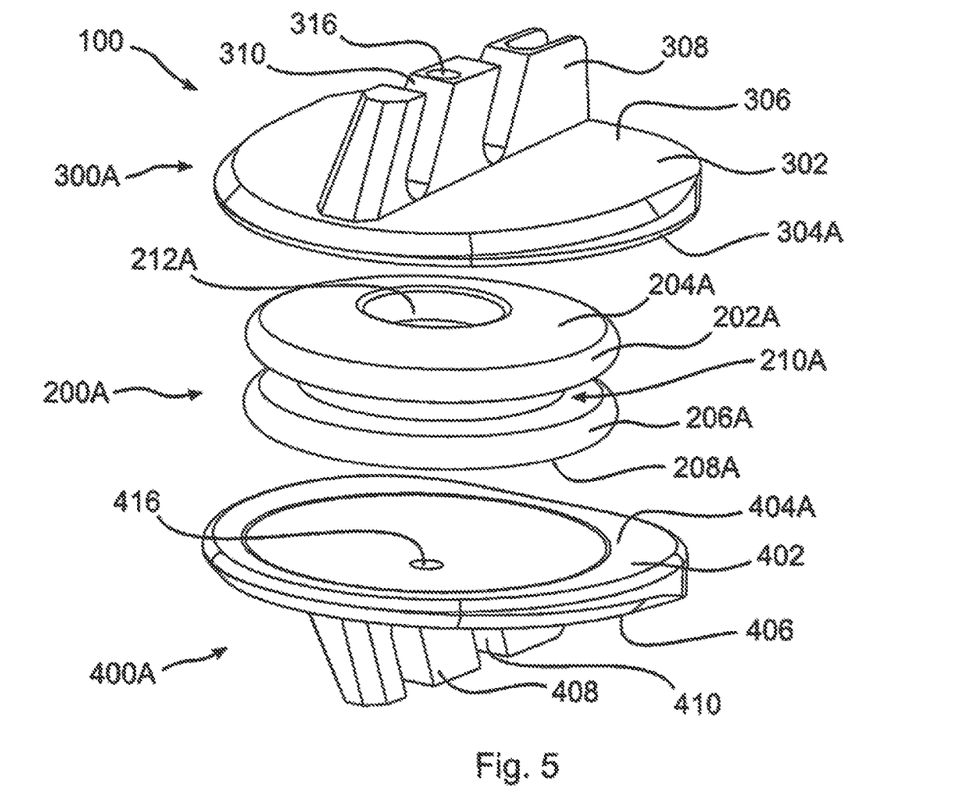
FIG. 5 depicts a perspective exploded view of another embodiment of an implant of the invention.
Figure 6:
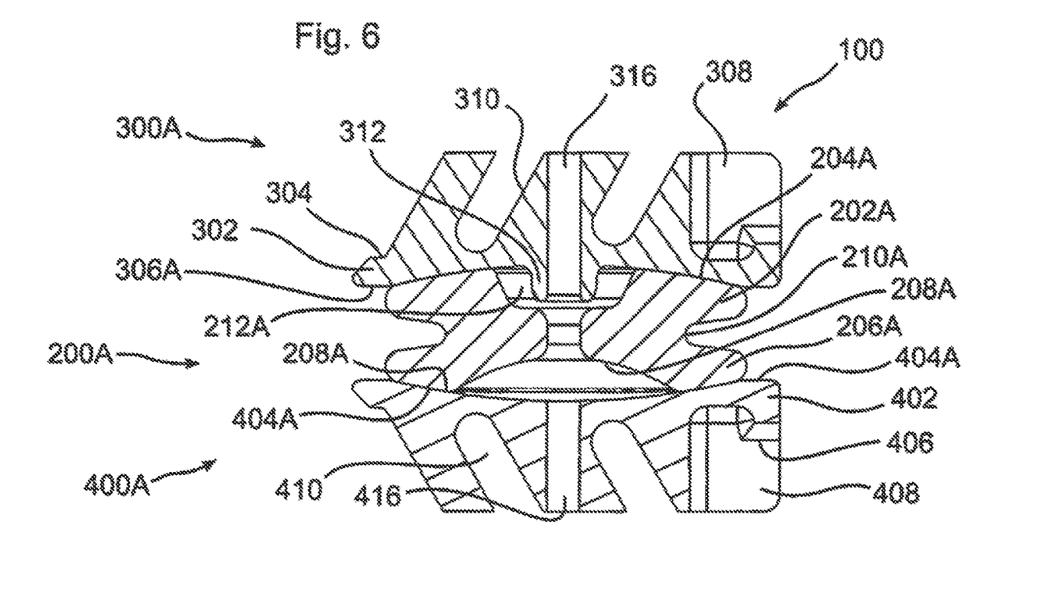
FIG. 6 illustrates a cross section of the implant of FIG. 5, taken centrally through bone engaging projections of the implant.

In an alternative embodiment, shown in FIGS. 5 and 6, core 200A includes first and second segments 202A, 206A, separated by an inflection region 210A that is substantially narrower than flanking segments 202A, 206A, and thus bends to enable an angular displacement of segments 202A, 206A, and accordingly enables an angular relative displacement of engaging surfaces 204A, 208A.

FIG. 6 illustrates a cross-section of the implant 100 of FIG. 5, taken through projections 308 and 408. At least a portion of core engaging surface 404A is configured as a curved smooth surface upon which a mating region of curved smooth surface of second engaging surface 208A of flexible core 200A may slide. In the illustration, a curved slidable portion of core engaging surface 404A is recessed within second support component 400A, and a mating slidable portion of engaging surface 208A projects from core 200A; however, it should be understood that engaging surface 404A may be projected, and engaging surface 208A may be recessed.

Similarly, a portion of first engaging surface 204A is a curved smooth surface upon which a mating curved smooth surface of core engaging surface 306A may slide. In the embodiment shown in FIGS. 5-6, core 200A forms two convex surfaces 204A, 208A, to foster a desired kinematic movement, and to maintain a desired ligament tension throughout the expected range of motion, and to promote a natural resting position of the bones. It should be understood, however, that in accordance with the invention, either surface 204A or 208A may be either convex or concave, as the therapeutic needs of the patient dictate. Alternatively, either surface may be flat, as illustrated in FIGS. 1-4, discussed above, or FIGS. 7-8, discussed below.

In one embodiment, a projection 312 extends from first engaging surface 306A into core aperture or hollow interior 212A, and is operative to limit an extent of movement of first support component 300 with respect to core 200. A similar configuration could be provided for slidably mating engaging surfaces 404A and 208A.

Embodiments of the invention may be provided with one or more apertures 316, 416 through which fasteners may be installed, to further secure implant 100 within a patient. For example, a bone screw may be passed through aperture 316 in first support component 300 and into bone 10, and another bone screw may be passed through aperture 416 in second support component 400, and into bone 12. A bone growth agent may alternatively or additionally be provided within aperture 316 or 416, or upon bone engaging surface 306 and or 406, to promote bone growth thereinto. Bone growth surfaces may be provided with openings or texture into which tissue may grow and adhere.

In use, the embodiment of FIGS. 5-6 enables all six degrees of movement as described above, however, due to the mating curved slidable engaging surfaces 208A and 404A, additional directional stability is provided, whereby sliding is inhibited to an extent in the absence of flexion or extension of the joint. This inhibition arises from a natural gravitational resting state of the mating curved engaging surfaces 208A and 404A.

Figure 7:
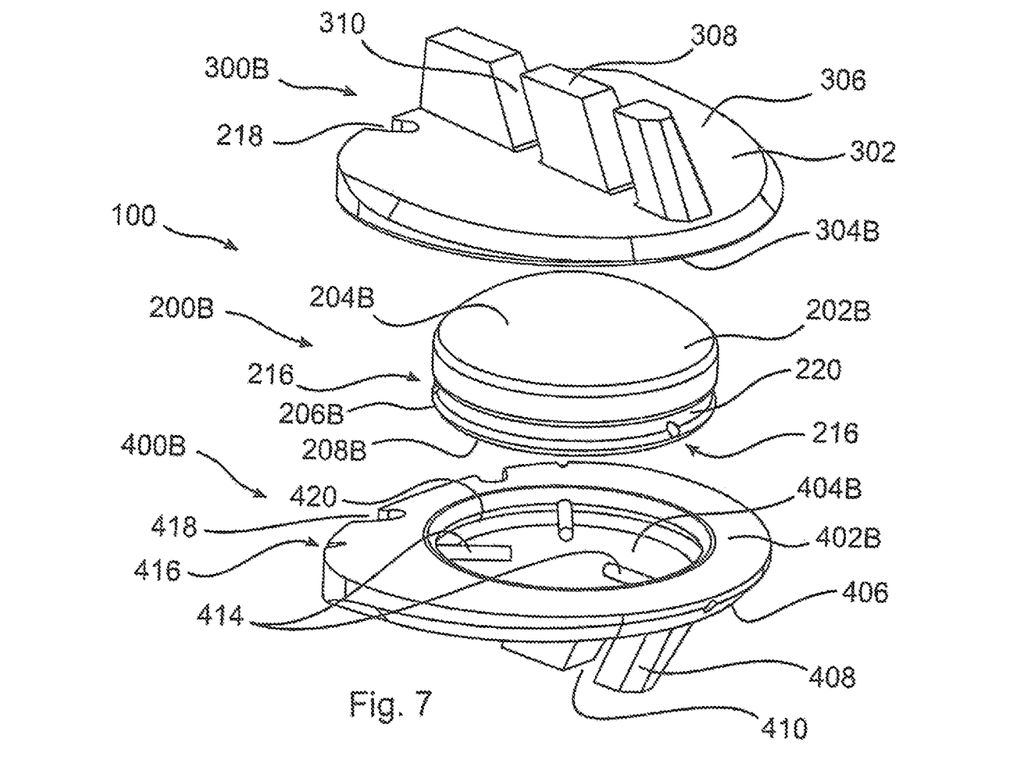
FIG. 7 depicts a perspective exploded view of a further embodiment of an implant of the invention; and, FIG. 8 illustrates a cross section of the implant of FIG. 7, taken centrally through bone engaging projections of the implant.
Figure 8:
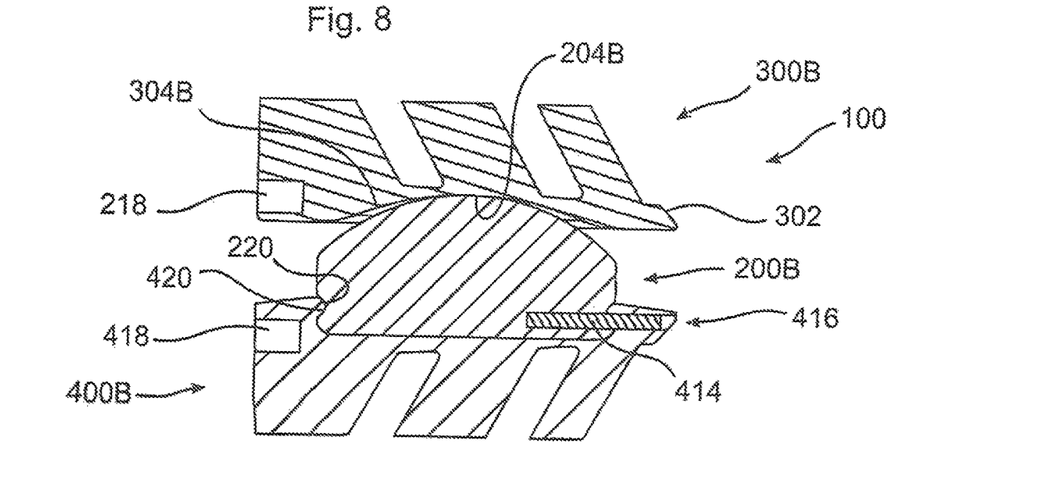

Referring now to the embodiment illustrated in FIGS. 7-8, in which core 200B is provided with a flat surface at second engaging surface 208B, matably connectable to flat core engaging surface 404B of second support component 400. In this embodiment, core 200B is configured to affix core 200B with respect to rotation upon second engaging surface 404B, by one or more pins 414, which pass through one or more pin bores or apertures 216, 416, provided in core 200B and second support component 400B, respectively. While pins are illustrated, it should be understood that other fastener configuration are possible, including screws, adhesive, set screws, interference fit, press fit, or other methods as would be understood by one skilled in the art. Pins 414 may be threaded or press fit into apertures 216 or 416, or secured using adhesive, and may be secured to either or both of core 200B or second support component 400B.

While pins 414 may be utilized to prevent rotation as well as to maintain core 200B in a position upon engagement surface 404B, an axial position of core 200B against engagement surface 404B may alternatively or additionally be maintained by a snap fit engagement between recessed portion 220 and projected portion 420 of core 200B and core engaging surface 404B, respectively. Alternatively, core 200B may be provided with a projecting portion, and core engaging surface 404B may be provided with a mating recess.

In any of the embodiments of the invention, should it be desired to maintain a position of either or both core engagement surfaces 304, 304A, 304B and 404, 404A, 404B relative to core 200, 200A, 200B, pins, a snap fit, or other fasteners may be used, as described above.

With further reference to FIG. 8, it can be seen that core engaging surface 304B has a curved portion having a radius which is larger than a curved portion of first engaging surface 204B. As such, core engaging surface 304B and first engaging surface 204B may readily slide, to a limited extent, relative to each other, as influenced by the difference between their respective curvatures. Core 200B may also be rotated, and compressed evenly or laterally, as detailed elsewhere herein with respect to other embodiments of the invention.

It should be understood that superior and inferior positions of components, as illustrated, are for the convenience of the reader in understanding the invention, and that implant 100 may be implanted in a reverse orientation than is shown, as benefits the patient.

In use, the embodiment of FIGS. 7-8 enables all six degrees of movement as described above, however, due to the mating curved slidable engaging surfaces 204B and 304B, additional directional stability is provided, whereby sliding is inhibited to an extent in the absence of flexion or extension of the joint. This inhibition arises from a natural gravitational resting state of the mating curved engaging surfaces 204B and 304B. Rotation, or spinning, of bone 10 with respect to bone 12, is translated only through an interface between first engaging surface 204B and core engaging surface 304B, as second engaging surface 208B is affixed with respect to core engaging surface 404B. Similarly, sliding is carried out solely through this interface, for the same reasons. Surfaces 208B and 404B may alternatively slide with respect to each other, as detailed herein with respect to other embodiments.

Mating surfaces 204, 204A, 204B and 304, 304A, 304B; or 208, 208A, 208B and 404, 404A, 404B, may, for example, be concave, convex, semi-spherical, elliptical, complex, or barrel shaped, whereby a resistance to sliding, spinning, rotating, rocking, or other relative movement may be uniform in all directions, or different in specific directions.

FIG. 8 further illustrates insertion tool channels, bores, openings, or apertures 218, 418, in first and second support components 300B, 400B. As implant 100 is inserted between joint surfaces maintained in spaced relation by ligaments, it may be necessary to mechanically compress implant 100 prior to insertion within the joint. A tool, not shown, such as is known in the art, may be provided with tines which engage tool apertures 218, 418, whereupon first and second support components 300B, 400B may be moved together, or apart, as determined by the practitioner, during implantation. Further, implant 100 may be implanted through an anterior, anterolateral, or lateral approach, and accordingly, tool apertures 218, 418 provide a means for mechanically grasping and manipulating implant 100 during implantation.

The invention provides a joint replacement implant, for example for replacement or stabilization of a cervical disc replacement, although other joints may be partially or completely replaced by implant 100, for example one or more joints of the fingers, hand, wrist, elbow, shoulder, other areas of the spine, hip, knee, ankle, foot, or toes.

Implant 100 is operative to restore the natural kinematic signature and natural joint properties, particularly for spinal discs, but for all joints which exhibit movement in all six degrees of motion, as detailed above.

All elements of implant 100 may be made from a flexible material, although core 200, in particular, flexes in order to accommodate an angular displacement of first and second support components 300, 400. As the joint is flexed or extended, the flexible and or resilient material of core 200 may bulge or stretch to enable an angular displacement of first and second engaging surfaces 204, 208. Additionally, or alternatively, inflection region 210 provides a relatively weaker region of core 200 which is adapted through thickness and or shape to facilitate bending of core 200.

Implant 100 may be fabricated using any biocompatible materials known to one skilled in the art, having sufficient strength, flexibility, resiliency, and durability for the patient, and for the term during which the device is to be implanted. Examples include but are not limited to metal, such as, for example titanium and chromium alloys; polymers, including for example, PEEK or high molecular weight polyethylene (HMWPE); and ceramics.

Portions or all of the implant may be radiopaque or radiolucent, or materials having such properties may be added or incorporated into the implant to improve imaging of the device during and after implantation.

Opposing mating surfaces which rotate, spin, or slide, including core engaging surfaces 304, 304A, 304B, 404, 404A, 404B, and first and second engaging surfaces 204, 204A, 204B and 208, 208A, 208B, may be made of the same or different materials, which combination produces a therapeutic fluidity of motion, or desired drag. Surfaces of implant 100 may be plasma sprayed, for example by titanium plasma spray, and may be bead blasted or electropolished.

More particularly, the support components may be manufactured from cobalt-chrome-molybdenum alloy, Co—Cr—Mo, as specified in ASTM F1537 (and ISO 5832-12). The smooth surfaces may be plasma sprayed with commercially pure titanium, as specified in ASTM F1580, F1978, F1147 and C-633 (and ISO 5832-2). The core may be manufactured from ultra-high molecular weight polyethylene, UHMWPE, as specified in ASTM F648 (and ISO 5834-2).

Core 200, 200A, 200B, may alternatively, in one embodiment, be fabricated using polycarbonate urethane (PCU), or a thermoplastic polycarbonate urethane (TPU) such as Bionate, a registered trademark of DSM IP Assets B.V. Corporation, of Heerlen Netherlands, for a thermoplastic elastomer formed as the reaction product of a hydroxyl terminated polycarbonate, an aromatic diisocyanate, and a low molecular weight glycol used as a chain extender. Other polymeric materials with suitable flexibility, durability, and biocompatibility may also be used, as understood by one skilled in the art.

In accordance with the invention, implants of various sizes may be provided to best fit the anatomy of the patient. Support components and a core of matching or divergent sizes may be assembled during the implantation procedure by a medical practitioner as best meets the therapeutic needs of the patient, the assembly inserted within the body using an insertion tool. Implants of the invention may also be provided with an overall angular geometry, for example angular mating dispositions of support components and core, to provide for a natural lordosis, or a corrective lordosis, for example of from 0° to 6° for a cervical application, although much different values may be advantageous for other joints. Implant heights, for use in the cervical vertebrae for example, may typically range from 7 mm to 12 mm, although the size is dependent on the patient, and the joint into which an implant of the invention is to be implanted.

In accordance with the invention, a single implant 100 may be used, to provide stabilization for a weakened joint or joint portion. Alternatively, two, three, or more implants 100 may be used, at a single joint level, or in multiple joints. Moreover, implants 100 may be combined with other stabilizing means.

Additionally, implant 100 may be fabricated using material that biodegrades in the body during a therapeutically advantageous time interval. Further, implant 100 is advantageously provided with smooth and or rounded exterior surfaces, which reduce a potential for deleterious mechanical effects on neighboring tissues.

Any surface or component of the invention may be coated with or impregnated with therapeutic agents, including bone growth, healing, antimicrobial, or drug materials, which may be released at a therapeutic rate, using methods known to those skilled in the art.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A method for stabilizing first and second bones in a patient, comprising: inserting an implant between the first and second bones, the implant including:

a first endplate having a first side adapted to be affixed to the first bone of the patient, and a second side opposite the first side, the second side having a first part of a snap fit mechanism, the first endplate having a plurality of projections adapted to be affixed to the first bone;

a resilient core having a third side and a second part of the snap fit mechanism such that the resilient core mates with the first endplate through the snap fit mechanism, the resilient core further including a fourth side opposite the third side, the fourth side having a convex surface having a first radius;

a second endplate having a fifth side engageable with the fourth side, and a sixth side opposite the fifth side adapted to be affixed to the second bone of the patient, the second endplate having a plurality of projections adapted to be affixed to the second bone, the fifth side having a recessed concave surface having a second radius larger than the first radius so as to provide a sliding motion relative to each other;

whereby a vertical axis of the implant is defined as extending from the first bone to the second bone;

whereby the core is positionable between the first and second endplates;

wherein the core separates the first and second endplates at a relative first distance along the vertical axis, the core being resiliently deformable under pressure to separate the first and second endplates at a second, lesser relative distance along the vertical axis;

wherein a plurality of pins extend from the second side of the first endplate substantially transverse to the vertical axis of the implant into the resilient core; and wherein when said first endplate is affixed to the first bone, and said second endplate is affixed to the second bone, and said core is positioned between said first and second endplates, the first and second bones are stabilized, and said core may both resiliently deform and slide separately or simultaneously, to enable six degrees of kinematic motion of the two bones similar to a natural kinematic movement of the bones.

2. The method of claim 1, wherein the resilient core includes thermoplastic material.

3. The method of claim 1, wherein the resilient core includes polycarbonate urethane material.

4. The method of claim 1, wherein the resilient core includes PEEK material.

5. The method of claim 1, wherein the second endplate and the resilient core each include PEEK material.

6. The method of claim 1, wherein a sidewall of each of the first and second endplates includes first and second tool apertures adapted to be grabbed by an insertion tool.

7. The method of claim 1, wherein the resilient core includes a recessed portion and a projected portion.

8. The method of claim 7, wherein the recessed portion and the projected portion are configured to provide a snap fit engagement.

9. The method of claim 1, wherein each of the plurality of pins is configured to be received in one of a plurality of apertures in the resilient core.

* * * * *